United States Patent
Ravishankar et al.

(10) Patent No.: US 10,441,944 B2
(45) Date of Patent: Oct. 15, 2019

(54) CATALYST COMPOSITION FOR ISOMERIZATION OF PARAFFINS

(71) Applicant: HINDUSTAN PETROLEUM CORPORATION LTD., Mumbai (IN)

(72) Inventors: Raman Ravishankar, Karnataka (IN); Safinaz Saif, Karnataka (IN); Sunil Mehla, Karnataka (IN); Bennet Chellian, Karnataka (IN); Peddy Venkatachallapathy Rao, Karnataka (IN); Choudary Venkateswarlu Nettem, Karnataka (IN); Sriganesh Gandham, Visakhapatnam (IN)

(73) Assignee: Hindustan Petroleum Corporation Ltd., Mumbai (IN)

( * ) Notice: Subject to any disclaimer, the term of this patent is extended or adjusted under 35 U.S.C. 154(b) by 454 days.

(21) Appl. No.: 14/969,966

(22) Filed: Dec. 15, 2015

(65) Prior Publication Data
US 2017/0001180 A1    Jan. 5, 2017

(30) Foreign Application Priority Data
Jun. 30, 2015 (IN) .......................... 2498/MUM/2015

(51) Int. Cl.
*B01J 23/04* (2006.01)
*B01J 23/40* (2006.01)
(Continued)

(52) U.S. Cl.
CPC ............... *B01J 29/24* (2013.01); *B01J 29/18* (2013.01); *B01J 29/22* (2013.01); *B01J 37/04* (2013.01);
(Continued)

(58) Field of Classification Search
CPC . B01J 23/04; B01J 23/40; B01J 23/755; B01J 23/892; B01J 27/186; B01J 29/24;
(Continued)

(56) References Cited

U.S. PATENT DOCUMENTS 3,153,678 A * 10/1964 Logemann ............... B01J 23/24
                                                585/268
4,356,316 A * 10/1982 Aoshima .................. C07C 45/35
                                                502/168
(Continued)

FOREIGN PATENT DOCUMENTS

EP    2 200 433       * 12/2008 ............... C01B 3/22
JP    05306240 A      * 11/1993 ............... C07C 9/12
JP    H0627078 B2     * 4/1994 ............... B01J 29/00

OTHER PUBLICATIONS

Palcheva et al., "The Effect of Nickel on the Component State and HDS Activity of Alumina-supported Heteropolytungstates", Kinetics and Catalysis, 2007, vol. 48, No. 6, pp. 847-852.*

Xu et al., "Skeletal Isomerization of n-Pentane over Platinum-Promoted Tungstophosphoric Acid Supported on MCM-4", 1Catal Lett (2008) 125: 83. https://doi.org/10.1007/s10562-008-9515-4, pp. 83-89.

(Continued)

*Primary Examiner* — Patricia L. Hailey
(74) *Attorney, Agent, or Firm* — Robert L. Stearns; Dickinson Wright, PLLC (57) ABSTRACT

A catalyst composition for isomerization of paraffins includes at least one metal, at least one heteropoly acid and a support material. Further provided are a process for preparation of the catalyst composition and a process for isomerization of paraffins using the catalytic composition.

33 Claims, 1 Drawing Sheet

(51) Int. Cl.

| | | |
|---|---|---|
| *B01J 23/755* | (2006.01) | |
| *B01J 29/26* | (2006.01) | |
| *B01J 29/42* | (2006.01) | |
| *B01J 29/48* | (2006.01) | |
| *B01J 29/61* | (2006.01) | |
| *B01J 29/64* | (2006.01) | |
| *B01J 29/24* | (2006.01) | |
| *B01J 29/18* | (2006.01) | |
| *C07C 5/27* | (2006.01) | |
| *B01J 29/22* | (2006.01) | |
| *B01J 37/08* | (2006.01) | |
| *B01J 37/04* | (2006.01) | |

(52) U.S. Cl.
CPC ............. *B01J 37/08* (2013.01); *C07C 5/2775* (2013.01); *C07C 2529/18* (2013.01); *C07C 2529/22* (2013.01); *C07C 2529/24* (2013.01)

(58) Field of Classification Search
CPC ... B01J 29/18; B01J 29/22; B01J 29/26; B01J 29/42; B01J 29/48; B01J 29/61; B01J 29/64; B01J 37/04; B01J 37/08; C07C 5/2775; C07C 2529/18; C07C 2529/22; C07C 2529/24
USPC ................ 502/150, 210, 211, 306, 313–317
See application file for complete search history.

(56) References Cited

U.S. PATENT DOCUMENTS

| | | | |
|---|---|---|---|
| 5,256,277 A | 10/1993 | Del Rossi et al. | |
| 5,420,092 A * | 5/1995 | Soled .................. | B01J 23/6527 502/210 |
| 5,576,256 A | 11/1996 | Monque et al. | |
| 2002/0148754 A1* | 10/2002 | Gong .................... | C10G 27/04 208/3 |
| 2004/0222132 A1 | 11/2004 | Zanibelli et al. | |
| 2006/0052240 A1* | 3/2006 | Sakai ...................... | B01J 23/44 502/202 |
| 2006/0094592 A1* | 5/2006 | Gillespie ................ | B01J 27/188 502/208 |
| 2006/0094919 A1* | 5/2006 | Gillespie ............. | B01J 23/6527 585/750 |
| 2006/0111591 A1* | 5/2006 | Fremy .................... | C07B 45/06 568/72 |
| 2013/0289319 A1* | 10/2013 | Allgeier ................. | C07C 29/60 568/861 |

OTHER PUBLICATIONS

Pérez-Luna et al., "n-Pentane Isomerization Over Pt- and Ni-Pt-Promoted Sulfated Zirconia Catalysts Supported on Alumina", Catal Lett (2009) 131: 285. https://doi.org/10.1007/s10562-009-0054-4, pp. 285-293.

* cited by examiner

CATALYST COMPOSITION FOR ISOMERIZATION OF PARAFFINS

BACKGROUND OF THE INVENTION

1. Technical Field

This U.S. Utility application claims priority to India Application No. 2498/MUM/2015, filed Jun. 30, 2015, and is incorporated herein by reference.

The subject matter described herein in general relates to a catalyst composition for isomerization of paraffins comprising of at least one metal, at least one heteropoly acid and a support material. The invention also relates to a process for the preparation of a catalyst composition for isomerization of paraffins. The invention further relates to a process for isomerization of paraffins using the catalytic composition.

2. Related Art

Isomerization of paraffins is important for the conversion of n-pentane and n-hexane into their respective isoparaffins of substantially higher octane number, and to provide additional feedstock for alkylation units. Several catalytic methods are known for paraffins isomerization. Skeletal isomerization of n-pentane in the presence of hydrogen has been studied over Pt-promoted $H_3PW_{12}O_{40}$ (TPA)/MCM-41 bifunctional catalyst. A series of solid acid catalysts with different loading amount of TPA and Pt were prepared and characterized by XRD, FT-IR and XPS. The optimal catalytic activity of Pt-TPA/MCM-41 was observed with 2% Pt and 30% TPA. According to the cracked products distribution, this is typical of a monomolecular bifunctional metal-acid mechanism. Further, catalysts with different combination of noble metals (Pt, Pd and Ru), heteropoly acids (HPAs) (TPA, tungstosilicic acid (TSA), and molybdophosphoric acid (MPA)) and supports (MCM-41, SBA-1 and $SiO_2$) were also synthesized and their catalytic performances were compared. (Xu, Yuandong, et al., Catalysis Letters, 125.1-2, 2008, 83-89.) In another report n-pentane isomerization over Pt- and Ni—Pt-promoted sulfated zirconia catalysts supported on alumina was studied in which two series of sulfated zirconia catalysts promoted with Pt and Pt—Ni, respectively, were prepared and extruded with different amount of alumina binder (0, 20, 33, and 60 wt %). The catalytic activities of the two series of catalysts, SZPtA and SZNiPtA, were measured for n-pentane isomerization reaction. The reaction reaches its maximum conversion at 20 wt % of alumina for both catalyst series. Adding alumina beyond 20 wt % reduces the overall conversion and modifies the selectivity for both catalysts series from i-C4 towards i-C5 suggesting that the reaction mechanism changed from a monomolecular to a bimolecular one. However, only SZNiPtA catalysts maintain a higher catalytic activity at higher amounts of alumina. Such difference between the two catalyst series can be attributed to the combining effect of Ni and Pt promotion of the SZNiPtA catalysts and not to their acidic properties. But it was seen that Zirconia deactivated at a faster rate however using Pt noble metal was expensive and the conversion was predominantly affected by the alumina content (Pérez-Luna, M., et al., Catalysis letters 131.1-2, 2009, 285-293.)

US20040222132 discloses a process for the upgrading of hydrocarbon mixtures which boil within the naphtha range containing sulfur impurities, i.e., a hydrodesulfuration process with contemporaneous skeleton isomerization and reduced hydrogenation degree of the olefins contained in said hydrocarbon mixtures, the whole process being carried out in a single step. The process is carried out in the presence of a catalytic system comprising a metal of group VI B, a metal of group VIII and a carrier of acid nature consisting of a mesoporoussilico-alumina.

U.S. Pat. No. 5,576,256 describes a hydroconversion catalyst composition including a catalytically active matrix having a surface area of between about 50 $m^2/g$ to about 290 $m^2/g$, a silicious molecular sieve support medium distributed through the matrix and having a surface area of between about 250 $m^2/g$ to about 1200 $m^2/g$ and a catalytically active phase supported on the support medium and including a first metal selected from group IIIA of the periodic table of elements and a second metal selected from group VIB of the periodic table of elements. The matrix preferably further includes aluminum, gallium, cobalt, molybdenum, and phosphorus.

U.S. Pat. No. 5,256,277 describes paraffins, especially paraffins in the $C_4$-$C_8$ range, which are isomerized to isoparaffins over an isomerization catalyst comprising a noble metal such as platinum on a support material comprising an inorganic, non-layered, porous, crystalline phase aluminosilicate material with pores of at least 13 Å and which exhibits, after calcination, an X-ray diffraction pattern with at least one peak at a d-spacing greater than 18 Å. These materials have a high surface area and sorption capacity marked by a benzene adsorption capacity of greater than about 15 grams benzene per 100 grams at 50 torr and 25° C. In its preferred form, the support material has a uniform, hexagonal arrangement of pores with diameters of at least about 13 Å and a hexagonal electron diffraction pattern that can be indexed with a $d_{100}$ value greater than about 18 Å which corresponds to at least one peak in the X-ray diffraction pattern.

SUMMARY

In an aspect of the present disclosure, there is provided a catalyst composition comprising at least one metal in an amount in the range of 0.1% to 10% w/w of the total weight of the composition; at least one heteropoly acid in an amount in the range of 14% to 50% w/w of the total weight of the composition; and a support material in an amount in the range of 60% to 85% w/w of the total weight of the composition.

In an aspect of the present disclosure, there is provided a process for producing a catalyst composition comprising at least one metal in an amount in the range of 0.1% to 10% w/w of the total weight of the composition; at least one heteropoly acid in an amount in the range of 14% to 50% w/w of the total weight of the composition; and a support material in an amount in the range of 60% to 85% w/w of the total weight of the composition, the process comprising dissolving at least one metal salt in water to obtain a solution; contacting at least one heteropoly acid and a support material with the solution to obtain a paste; drying the paste to obtain a dried paste; and calcining the dried paste at a temperature range of 400-600° C. for a period of 1 to 6 hours to obtain a catalyst composition.

In an aspect of the present disclosure, there is provided a process for isomerization of paraffins comprising contacting the paraffins and hydrogen with a catalyst composition in a reactor; wherein the catalyst composition comprises of at least one metal in an amount in the range of 0.1% to 10% w/w of the total weight of the composition; at least one heteropoly acid in an amount in the range of 14% to 50% w/w of the total weight of the composition; and a support material in an amount in the range of 60% to 85% w/w of the total weight of the composition.

These and other features, aspects, and advantages of the present subject matter will be better understood with reference to the following description and appended claims. This summary is provided to introduce a selection of concepts in a simplified form. This summary is not intended to identify key features or essential features of the claimed subject matter, nor is it intended to be used to limit the scope of the claimed subject matter.

BRIEF DESCRIPTION OF ACCOMPANYING DRAWINGS

The following drawings form part of the present specification and are included to further illustrate aspects of the present disclosure. The disclosure may be better understood by reference to the drawings in combination with the detailed description of the specific embodiments presented herein.

DETAILED DESCRIPTION

Those skilled in the art will be aware that the present disclosure is subject to variations and modifications other than those specifically described. It is to be understood that the present disclosure includes all such variations and modifications. The disclosure also includes all such steps, features, compositions and compounds referred to or indicated in this specification, individually or collectively and any and all combinations of any or more of such steps or features.

Definitions

For convenience, before further description of the present disclosure, certain terms employed in the specification, and examples are collected here. These definitions should be read in the light of the remainder of the disclosure and understood as by a person of skill in the art. The terms used herein have the meanings recognized and known to those of skill in the art, however, for convenience and completeness, particular terms and their meanings are set forth below.

The articles "a", "an" and "the" are used to refer to one or to more than one (i.e., to at least one) of the grammatical object of the article.

The terms "comprise" and "comprising" are used in the inclusive, open sense, meaning that additional elements may be included. Throughout this specification, unless the context requires otherwise the word "comprise", and variations, such as "comprises" and "comprising", will be understood to imply the inclusion of a stated element or step or group of element or steps but not the exclusion of any other element or step or group of element or steps.

The term "catalyst composite(s)" and "catalyst composition(s)" are used interchangeably in the present disclosure.

Ratios, concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited.

In an embodiment of the present disclosure, there is provided a catalyst composition comprising at least one metal in an amount in the range of 0.1% to 10% w/w of the total weight of the composition; at least one heteropoly acid in an amount in the range of 14% to 50% w/w of the total weight of the composition; and a support material in an amount in the range of 60% to 85% w/w of the total weight of the composition.

In an embodiment of the present disclosure, there is provided a catalyst composition as described herein, wherein the at least one metal is selected from the group consisting of alkali metal, alkaline earth metal, transitional metal, lanthanides, and combinations thereof.

In an embodiment of the present disclosure, there is provided a catalyst composition as described herein, wherein the at least one metal is selected from the group consisting of Na, K, Rb, Cs, and combinations thereof.

In an embodiment of the present disclosure, there is provided a catalyst composition as described herein, wherein the at least one metal is selected from the group consisting of a combination of Na—K, Na—Rb, Na—Cs, K—Rb, K—Cs, and Rb—Cs.

In an embodiment of the present disclosure, there is provided a catalyst composition as described herein, wherein the at least one metal is selected from the group consisting of Pt, Ni, Pd, Re, Ir, Rh, and combinations thereof.

In an embodiment of the present disclosure, there is provided a catalyst composition as described herein, wherein the at least one metal is selected from the group consisting of a combination of Pt—Ni, Pt—Pd, Pt—Re, Pt—Ir, Pt—Rh, Ni—Pd, Ni—Re, Ni—Ir, Ni—Rh, Pd—Re, Pd—Ir, Pd—Rh, Re—Ir, Re—Rh, and Ir—Rh.

In an embodiment of the present disclosure, there is provided a catalyst composition as described herein, wherein the at least one metal is in an amount in the range of 0.1% to 6% w/w of the total weight of the composition.

In an embodiment of the present disclosure, there is provided a catalyst composition as described herein, wherein the at least one metal is in an amount in the range of 1.5% to 6% w/w of the total weight of the composition.

In an embodiment of the present disclosure, there is provided a catalyst composition as described herein, wherein the at least one metal can be in an amount of 1.5%, 2%, 2.5%, 3%, 3.5%, 4%, 4.5%, 5%, 5.5% or 6% w/w of the total weight of the composition.

In an embodiment of the present disclosure, there is provided a catalyst composition as described herein, wherein the at least one metal is nickel in an amount range of 1.5% to 6% w/w of the total weight of the composition.

In an embodiment of the present disclosure, there is provided a catalyst composition as described herein, wherein the heteropoly acid is selected from the group consisting of tungstophosphoric acid (TPA), molybdophosphoric acid (MPA), and combinations thereof.

In an embodiment of the present disclosure, there is provided a catalyst composition as described herein, wherein the heteropoly acid is in an amount in the range of 18% to 30% w/w of the total weight of the composition.

In an embodiment of the present disclosure, there is provided a catalyst composition as described herein, wherein the heteropoly acid can be in an amount of 18%, 19%, 20%, 21%, 22%, 23%, 24%, 25%, 26%, 27%, 28%, 29% or 30% w/w of the total weight of the composition.

In an embodiment of the present disclosure, there is provided a catalyst composition as described herein, wherein the at least one heteropoly acid is tungstophosphoric acid (TPA) in an amount in the range of 18% to 30% w/w of the total weight of the composition.

In an embodiment of the present disclosure, there is provided a catalyst composition as described herein, wherein the support material is selected from the group consisting of alumina, zirconia, titania, silica, niobia, zeolites, mesoporous oxides, microporous oxides, ceria, vanadia, magnesia, yttria, and mesoporous materials such as MCM-41, MCM-48, and SBA-15.

In an embodiment of the present disclosure, there is provided a catalyst composition as described herein, wherein the support material is in an amount in the range of 70% to 80% w/w of the total weight of the composition.

In an embodiment of the present disclosure, there is provided a catalyst composition as described herein, wherein the support material can be in an amount of 70%, 71%, 72%, 73%, 74%, 75%, 76%, 77%, 78%, 79% or 80% w/w of the total weight of the composition.

In an embodiment of the present disclosure, there is provided a catalyst composition as described herein, wherein the support material is a zeolite selected from the group consisting of USY-zeolite, ZSM-5, ZSM-11, mordenite, and beta zeolite.

In an embodiment of the present disclosure, there is provided a catalyst composition as described herein, wherein the support material is mordenite in an amount in the range of 70% to 80% w/w of the total weight of the composition.

In an embodiment of the present disclosure, there is provided a catalyst composition as described herein, wherein the at least one metal is in an amount in the range of 0.1% to 10% w/w of the total weight of the composition and is selected from the group consisting of alkali metal, alkaline earth metal, transitional metal, lanthanides, and combinations thereof; the at least one heteropoly acid is in an amount in the range of 14% to 50% w/w of the total weight of the composition and is selected from the group consisting of tungstophosphoric acid (TPA), molybdophosphoric acid (MPA), and combinations thereof; and the support material is in an amount in the range of 60% to 85% w/w of the total weight of the composition and is selected from the group consisting of alumina, zirconia, titania, silica, niobia, zeolites, mesoporous oxides, microporous oxides, ceria, vanadia, magnesia, yttria, and mesoporous materials such as MCM-41, MCM-48, and SBA-15.

In an embodiment of the present disclosure, there is provided a catalyst composition as described herein, wherein the at least one metal is in an amount in the range of 1.5% to 6% w/w of the total weight of the composition and is selected from the group consisting of Na, K, Rb, Cs, and combinations thereof; the at least one heteropoly acid is in an amount in the range of 18% to 30% w/w of the total weight of the composition and is selected from the group consisting of tungstophosphoric acid (TPA), molybdophosphoric acid (MPA), and combinations thereof; and the support material is in an amount in the range of 70% to 80% w/w of the total weight of the composition and is a zeolite selected from the group consisting of USY-zeolite, ZSM-5, ZSM-11, mordenite, and beta zeolite.

In an embodiment of the present disclosure, there is provided a catalyst composition as described herein, wherein the at least one metal is in an amount in the range of 1.5% to 6% w/w of the total weight of the composition and is selected from the group consisting of Pt, Ni, Pd, Re, Ir, Rh, and combinations thereof; the at least one heteropoly acid is in an amount in the range of 18% to 30% w/w of the total weight of the composition and is selected from the group consisting of tungstophosphoric acid (TPA), molybdophosphoric acid (MPA), and combinations thereof; and the support material is in an amount in the range of 70% to 80% w/w of the total weight of the composition and is a zeolite selected from the group consisting of USY-zeolite, ZSM-5, ZSM-11, mordenite, and beta zeolite.

In an embodiment of the present disclosure, there is provided a catalyst composition as described herein, wherein the at least one metal is nickel in an amount in the range of 1.5% to 6% w/w of the total weight of the composition; the at least one heteropoly acid is tungstophosphoric acid (TPA) in an amount in the range of 18% to 30% w/w of the total weight of the composition; and the support material is mordenite in an amount in the range of 70% to 80% w/w of the total weight of the composition.

In an embodiment of the present disclosure, there is provided a catalyst composition as described herein, wherein the catalyst composition is 1.5% to 6% w/w Ni, 18% to 30% w/w tungstophosphoric acid (TPA), and 70% to 80% w/w mordenite.

In an embodiment of the present disclosure, there is provided a catalyst composition as described herein, wherein the catalyst is used for isomerization of paraffins.

In an embodiment of the present disclosure, there is provided a process for producing a catalyst composition as described herein, the process comprising dissolving at least one metal salt in water to obtain a solution; contacting at least one heteropoly acid and a support material with the solution to obtain a paste; drying the paste to obtain a dried paste; and calcining the dried paste at a temperature range of 400-600° C. for a period of 1 to 6 hours to obtain a catalyst composition.

In an embodiment of the present disclosure, there is provided a process for producing a catalyst composition as described herein, the process comprising dissolving at least one metal salt in water to obtain a solution; contacting at least one heteropoly acid and a support material with the solution to obtain a paste; drying the paste in vacuum for a period of 2-3 hours at a temperature range of 50 to 90° C. and at 100 mbar pressure to obtain a dried paste; and calcining the dried paste at a temperature range of 400-600° C. for a period of 1 to 6 hours to obtain a catalyst composition.

In an embodiment of the present disclosure, there is provided a process for producing a catalyst composition as described herein, wherein the at least one metal salt is a salt of a metal selected from the group consisting of alkali metal, alkaline earth metal, transitional metal, and combinations thereof.

In an embodiment of the present disclosure, there is provided a process for producing a catalyst composition as described herein, wherein the at least one metal salt is a salt of Ni selected from the group consisting of nickel nitrate, nickel chloride, nickel acetate, nickel sulphate, and nickel acetylacetonate.

In an embodiment of the present disclosure, there is provided a process for producing a catalyst composition as described herein, wherein at least one metal salt is a salt of Pt selected from the group consisting of platinum nitrate, platinum chloride, platinum acetate, chloroplatinic acid and platinum complexes such as hexamine platinum II chloride.

In an embodiment of the present disclosure, there is provided a process for producing a catalyst composition as described herein, wherein at least one metal salt is a salt of Cs selected from the group consisting of cesium nitrate, cesium chloride, cesium acetate, and cesium sulfate.

In an embodiment of the present disclosure, there is provided a process for producing a catalyst composition as described herein, wherein the at least one heteropoly acid is selected from the group consisting of tungstophosphoric acid (TPA), molybdophosphoric acid (MPA), and combinations thereof.

In an embodiment of the present disclosure, there is provided a process for producing a catalyst composition as described herein, wherein the support material is selected from the group consisting of alumina, zirconia, titania, silica, niobia, zeolites, mesoporous oxides, microporous oxides, ceria, vanadia, magnesia, yttria, and mesoporous materials such as MCM-41, MCM-48, and SBA-15.

In an embodiment of the present disclosure, there is provided a process for producing a catalyst composition as described herein, wherein the support material is a zeolite selected from the group consisting of USY-zeolite, ZSM-5, ZSM-11, mordenite, and beta zeolite.

In an embodiment of the present disclosure, there is provided a process for producing a catalyst composition as described herein, wherein the support material is selected from the group consisting of titania, and mordenite.

In an embodiment of the present disclosure, there is provided a process for producing a catalyst composition as described herein, wherein the catalyst composition is at least one metal in an amount in the range of 1.5% to 6% w/w of the total weight of the composition, at least one heteropoly acid in an amount in the range of 18% to 30% w/w of the total weight of the composition, and support material in an amount in the range of 70% to 80% w/w of the total weight of the composition.

In an embodiment of the present disclosure, there is provided a process for producing a catalyst composition, the process comprising the steps of dissolving nitrate salt of Ni in water to obtain a solution; contacting tungstophosphoric acid (TPA), and mordenite with the solution to obtain a paste; drying the paste in vacuum at 70° C. for 1 hr at 100 mbar pressure to obtain a dried paste; and calcining the dried paste at 300° C. for 4 h to obtain a catalyst composition.

In an embodiment of the present disclosure, there is provided a process for isomerization of paraffins comprising contacting the paraffins and hydrogen with a catalyst composition in a reactor; wherein the catalyst composition comprises of at least one metal in an amount in the range of 0.1% to 10% w/w of the total weight of the composition; at least one heteropoly acid in an amount in the range of 14% to 50% w/w of the total weight of the composition; and a support material in an amount in the range of 60% to 85% w/w of the total weight of the composition.

In an embodiment of the present disclosure, there is provided a process for isomerization of paraffins as described herein, wherein the at least one metal is selected from the group consisting of alkali metal, alkaline earth metal, transitional metal, and combinations thereof.

In an embodiment of the present disclosure, there is provided a process for isomerization of paraffins as described herein, wherein the at least one heteropoly acid is selected from the group consisting of tungstophosphoric acid (TPA), molybdophosphoric acid (MPA), and combinations thereof.

In an embodiment of the present disclosure, there is provided a process for isomerization of paraffins as described herein, wherein the support material is selected from the group consisting of alumina, zirconia, titania, silica, niobia, zeolites, mesoporous oxides, microporous oxides, ceria, vanadia, magnesia, yttria, and mesoporous materials such as MCM-41, MCM-48, and SBA-15.

In an embodiment of the present disclosure, there is provided a process for isomerization of paraffins as described herein, wherein the at least one metal salt is in an amount in the range of 0.1% to 6% w/w of the total weight of the composition.

In an embodiment of the present disclosure, there is provided a process for isomerization of paraffins as described herein, wherein the at least one metal is in an amount in the range of 1.5% to 6% w/w of the total weight of the composition.

In an embodiment of the present disclosure, there is provided a process for isomerization of paraffins as described herein, wherein the at least one heteropoly acid is in an amount in the range of 18% to 30% w/w of the total weight of the composition.

In an embodiment of the present disclosure, there is provided a process for isomerization of paraffins as described herein, wherein the support material is in an amount in the range of 70% to 80% w/w of the total weight of the composition.

In an embodiment of the present disclosure, there is provided a process for isomerization of paraffins as described herein, wherein the catalyst composition is 1.5% to 6% w/w Ni, 18% to 30% w/w tungstophosphoric acid (TPA), and 70% to 80% w/w mordenite.

In an embodiment of the present disclosure, there is provided a process for isomerization of paraffins as described herein, wherein the paraffin is a refinery feedstock such as straight run naphtha, cracked run naptha and fcc naphtha.

In an embodiment of the present disclosure, there is provided a process for isomerization of paraffins as described herein, wherein the paraffin is $C_5$ to $C_{10}$ linear paraffin.

In an embodiment of the present disclosure, there is provided a process for isomerization of paraffins as described herein, wherein hydrogen is passed over the catalyst composition at a rate of 10-100 mL/min.

In an embodiment of the present disclosure, there is provided a process for isomerization of paraffins as described herein, wherein hydrogen is passed over the catalyst composition at a rate of 1 mL/min.

In an embodiment of the present disclosure, there is provided a process for isomerization of paraffins as described herein, wherein the process is carried out at a temperature in the range of 150-370° C.

In an embodiment of the present disclosure, there is provided a process for isomerization of paraffins as described herein, wherein the process is carried out at a temperature in the range of 150-300° C.

In an embodiment of the present disclosure, there is provided a process for isomerization of paraffins as described herein, wherein the process is carried out at a temperature of 250° C.

In an embodiment of the present disclosure, there is provided a process for isomerization of paraffins as described herein, wherein the process is carried out at a pressure in the range of 5-50 bar.

In an embodiment of the present disclosure, there is provided a process for isomerization of paraffins as described herein, wherein the process is carried out at a pressure of 30 bar.

In an embodiment of the present disclosure, there is provided a process for isomerization of paraffins as described herein, wherein the paraffin weight hourly space velocity is in the range of 0.01 to 100 $hr^{-1}$.

In an embodiment of the present disclosure, there is provided a process for isomerization of paraffins as described herein, wherein the paraffin weight hourly space velocity is 2 hr$^{-1}$.

In an embodiment of the present disclosure, there is provided a process for isomerization of paraffins as described herein, wherein the catalyst composition is reduced in hydrogen flow of 35 ml/min at 300° C. for 2 h.

In an embodiment of the present disclosure, there is provided a process for isomerization of paraffins as described herein, wherein the feedstock is n-hexane and process is carried out in an automatic fixed bed downflow reactor with the heating tracing of the fee and product lines prior to and after the reactor at a temperature of 300° C., 30 bar pressure, hydrogen flow of 35 ml/min and paraffin weight hourly space velocity of 2 hr$^{-1}$, and wherein the catalyst composition is reduced in hydrogen flow of 35 ml/min at 300° C. for 2 h prior to the reaction.

Although the subject matter has been described in considerable detail with reference to certain embodiments thereof, other embodiments are possible.

EXAMPLES

The following examples are given by way of illustration of the present invention and should not be construed to limit the scope of present disclosure. It is to be understood that both the foregoing general description and the following detailed description are exemplary and explanatory only and are intended to provide further explanation of the claimed subject matter.

Example 1

Preparation of Tungstophosphoric Acid:

Tungstophosphoric acid (TPA) was prepared by the following method.

To 150 mL of deionized water, $Na_2WO_4 \cdot 2H_2O$ (26.39 g) and $Na_2HPO_4 \cdot 12H_2O$ (3.39 g) were added and the mixture was refluxed at 363K for around 2-3 h. This was followed by drop wise addition of 20% HCl till a pH value about 1-2. The residual solution was shaken vigorously with ether and concentrated HCl. The adduct formed with ether, which settled down at the bottom, was separated from the aqueous phase. The yellow crystals of TPA were dried at 110° C. and calcined at 300° C. for 4 hours.

Figure 1:
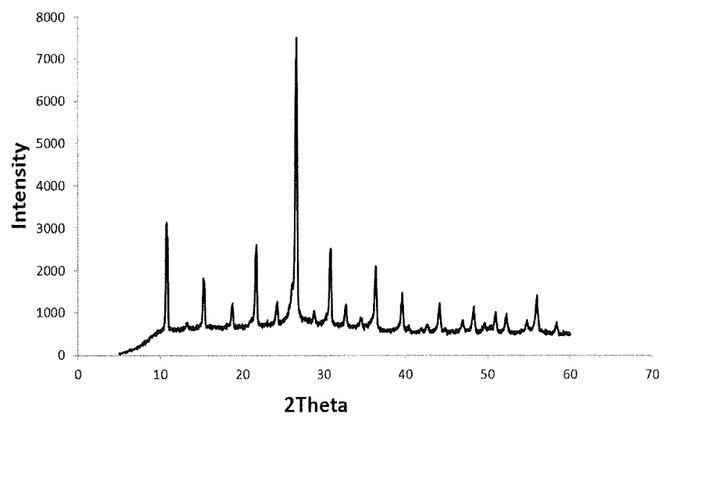
FIG. 1 depicts the X-ray Diffraction (XRD) plot of molybdophosphoric acid (MPA).

Preparation of Molybdophosphoric Acid:

Molybdophosphoric acid (MPA) was prepared by the following method. 0.628 g conc. phosphoric acid dissolved in 32 ml water is added to 6.3 g of Ammoniumhetamolybdate dissolved in 31 ml water and mixed thoroughly. This was followed by drop wise addition of 20% HCl till a pH value about 1-2 and precipitation stops. The precipitate is filtered and washed with acetone. The obtained yellow crystals are dried overnight at 110° C. and calcined at 300° C. for 4 hours. For characterization of MPA X-ray Diffraction analysis was done. FIG. 1 shows the XRD plot of MPA.

Preparation of MCM-41:

20.045 g of Cetyltrimethylamoniumbromide (CTAB) dissolved in 250 ml water and 11.5 g of ethanol dissolved in 200 ml water were mixed with each other slowly and thoroughly. 200 g of 25% Ammonia solution and 0.697 g of sodium acetate dissolved in 250 ml water was added to the above mixture slowly. Finally 52 g of tetraethylorthosilicate (TEOS) is added to the above mixture slowly and stirred for 2.5 hours and aged at 70° C. for 5 hours. The resulting gel is filtered and the precipitate collected is dried overnight at 110° C. and calcined at 550° C. for 6 hours.

Preparation of X % Metal Salts of MPA:

X % metal salt of MPA was prepared by wet impregnation of metal nitrate solution corresponding to X g of metal on 100 g of molybdophosphoric acid and vacuum drying. The resulting material was calcined at 300° C. for 4 hours. Nickel-MPA, Cesium-MPA, Platinum-MPA were prepared in this manner.

Preparation of X % Metal Salts of TPA:

X % metal salt of TPA was prepared by wet impregnation of metal nitrate solution corresponding to X g of metal on 100 g of tungstophosphoric acid and vacuum drying. The resulting material was calcined at 300° C. for 4 hours. Nickel-TPA and Platinum-TPA were prepared in this manner.

Preparation of X % Metal-TPA (Y)-Mordenite (Z) Composite:

The composite with Mordenite was made by wet impregnation of a Y g solution of the respective X % metal salt of TPA with Z g Mordenite (SAR 20) and vacuum drying. The resulting material was calcined at 300° C. for 4 hours.

Preparation of X % Metal-MPA (Y)-Mordenite (Z) Composite:

The composite with Mordenite was made by wet impregnation of a Y g solution of the respective X % metal salt of MPA with Z g Mordenite (SAR 20) and vacuum drying. The resulting material was calcined at 300° C. for 4 hours. For example: 0.0238 g Pt-salt was dissolved in 40 ml deionized water. 4 g Mordenite was added to the solution and pH was maintained above 10. The slurry was stirred at 25° C. for 3 days, filtered and dried at 110° C. for 2 h. The sample was calcined at 550° C. for 4 hours. 2 g of TPA was taken in 30 ml water and 8 gm titania powder is added and made as a slurry. The slurry was heated to 50° C. for 2 hours and dried under vacuum (120 mtorr). 0.0575 g TetramminePt(II) nitrate was dissolved in 30 ml water and TPA-Titania composite was added to the Pt-solution and stirred for 2 hours at 50° C. and dried under vacuum (120 mtorr). The resulting composite was calcined at 300° C. for 4 hours. Instead of titania powder, Mordenite was used for making metal-TPA-Mordenite composite.

Table 1 below details the composition of various catalytic composites of the present disclosure, wherein X denotes metal, Y denotes heteropoly acid, Z denotes support material, MOR stands for mordenite, TPA stands for tungstophosphoric acid, and MPA stands for molybdophosphoric acid.

TABLE 1

| S. NO. | Catalyst Code | X-Metal % (wt. of X/ gm of Y) | Y (TPA/ MPA%) | Z (Mordenite (20)%) |
|---|---|---|---|---|
| 1 | 0.3% Pt-MOR | 0.3 (0.023 g) | 0 | 0 |
| 2 | 0.3% Pt-MOR | 0.3 (0.023 g) | 0 | 0 |
| 3 | 0.3% Pt-MOR | 0.3 (0.023 g) | 0 | 0 |

TABLE 1-continued

| S. NO. | Catalyst Code | X-Metal % (wt. of X/gm of Y) | Y (TPA/MPA%) | Z (Mordernite (20)%) |
|---|---|---|---|---|
| 4 | 0.3% Pt-MOR | 0.3 (0.023 g) | 0 | 0 |
| 5 | 4.067% Ni-TPA(30)-MOR(100) | 5(0.0509 in 1 g) | 30 | 100 |
| 6 | 4.067% Ni-TPA(30)-MOR(100) | 5(0.0509 in 1 g) | 30 | 100 |
| 7 | 5% Ni-TPA(20)-TiO$_2$(80) | 5 | 20 | 80 |
| 8 | 0.3Pt-MPA(20)-MOR(100) | 0.3(0.003 g in 1 g) | 20 | 100 |
| 9 | 0.3% Ni-MPA(20)-MOR(100) | 0.3(0.003 g in 1 g) | 20 | 100 |
| 10 | 5% Ni-TPA(30)-MOR(70) | 5 | 30 | 70 |
| 11 | 0.3% Cs-MPA(16)-MOR(84) | 0.3(0.003 in 1 g) | 16 | 84 |
| 12 | 2.5% Ni-TPA(30)-MOR(100) | 2.5(0.025 in 1 g) | 30 | 100 |
| 13 | 5.7490% Ni-MPA(30)-MOR(100) | 5(0.0803 in 1 g) | 30 | 100 |
| 14 | 7.5% Ni-TPA(30)-MOR(100) | 7.5(0.075 in 1 g) | 30 | 100 |
| 15 | 0.3% Pt-TPA(30)-MOR(100) | 0.3(0.003 in 1 g) | 30 | 100 |
| 16 | TPA(30)-MOR(100) | 0 | 30 (0.3 in 1 g) | 100 |
| 17 | 5% Ni on MOR | 5(0.05 in 1 g) | 0 | 100 |
| 18 | 4.067% Ni-TPA(30)-MOR(100) | 5(0.0509 in 1 g) | 30 | 100 |
| 19 | 4.067% Ni-TPA(30)-MOR(100) | 5(0.0509 in 1 g) | 30 | 100 |
| 20 | 4.067% Ni-TPA(30)-MOR(100) | 5(0.0509 in 1 g) | 30 | 100 |

Process for Isomerization of Paraffins:

The isomerization reactions were carried out in a completely automatic fixed bed downflow reactor with the heating tracing of the feed and product lines prior to and after the reactor. The catalyst loading was 1-2 gm. The catalyst was reduced in hydrogen flow of 35 ml/min at the 300° C. for 2 hours prior to the reaction. The reactor was pressurized with hydrogen. Pt/MOR catalyst was synthesized as a reference and reactions conditions were optimized with respect to pressure, temperature and weight hourly space velocity (WHSV). N-hexane as the feedstock, a temperature of 250° C., 30 bar pressure, H$_2$ flow of 35 ml/min and WHSV 2 h$^{-1}$ were chosen as the evaluation conditions for all other catalysts. The product distribution was recorded using a Detailed Hydrocarbon Analyzer following the ASTM procedure. Table 2 below shows the comparison of different catalyst compositions, wherein MOR stands for mordenite, TPA stands for tungstophosphoric acid, MPA stands for molybdophosphoric acid, 22DMB stands for 2,2-dimethylbutane, and 23DMB stands for 2,3-dimethylbutane.

TABLE 2

| S. No. | Catalyst | Temperature (° C.) | Conversion (%) | Selectivity (%) | 22DMB iso ratio | 23DMB iso ratio |
|---|---|---|---|---|---|---|
| 1 | 0.3% Pt-MOR | 250 | 14.58 | 91.14 | 2.32 | 12.74 |
| 2 | 0.3% Pt-MOR | 270 | 32 | 98.33 | 3.63 | 12.83 |
| 3 | 0.3% Pt-MOR | 290 | 59.49 | 98.03 | 6.00 | 12.72 |
| 4 | 0.3% Pt-MOR | 310 | 77.6 | 93.41 | 11.23 | 12.03 |
| 5 | 5% Ni-TPA(30)-MOR(100) | 250 | 53.24 | 95.04 | 10.65 | 13.07 |
| 6 | 5% Ni-TPA(30)-MOR(100) | 250 | 49.4 | 96.05 | 9.44 | 13.04 |
| 7 | 5% Ni-TPA(20)-TiO$_2$(80) | 250 | 21.39 | 97.64 | 3.44 | 12.88 |
| 8 | 0.3Pt-MPA(20)-MOR(100) | 250 | 10.88 | 97.18 | 9.42 | 16.39 |
| 9 | 0.3% Ni-MPA(20)-MOR(100) | 250 | 1.77 | 85.65 | 6.99 | 14.1 |
| 10 | 5% Ni-TPA(30)-MOR(70) | 250 | 1.66 | 85.88 | 5.04 | 12.48 |
| 11 | 0.3% Cs-MPA(16)-MOR(84) | 250 | 1.64 | 83.03 | 6.15 | 13.25 |
| 12 | 2.5% Ni-TPA(30)-MOR(100) | 250 | 7.79 | 90.96 | 8.01 | 13.89 |
| 13 | 5% Ni-MPA(30)-MOR(100) | 250 | 2.8 | 91.47 | 1.32 | 6.5 |

TABLE 2-continued

| S. No. | Catalyst | Temperature (° C.) | Conversion (%) | Selectivity (%) | 22DMB iso ratio | 23DMB iso ratio |
|---|---|---|---|---|---|---|
| 14 | 7.5% Ni-TPA(30)-MOR(100) | 250 | 23.35 | 97.67 | 6.45 | 13.13 |
| 15 | 0.3% Pt-TPA(30)-MOR(100) | 250 | 33.72 | 97.94 | 10.82 | 13.12 |
| 16 | TPA(30)-MOR(100) | 250 | 2.22 | 77.43 | 1.25 | 3.03 |
| 17 | 5% Ni on MOR | 250 | 6.6 | 86.48 | 3.66 | 9.26 |

As seen in Table 2 catalyst compositions formed by various combination of metal salt, heteropoly acid and support material shows different isomerizing activity. At optimized temperature of 250° C., catalyst composition without heteropoly acid shows low isomerization activity as observed by low conversion percentage and disproportionate isomer ratio. However, with increase in temperature the conversion rate increases and isomer ratio also becomes proportionate. Similarly catalyst compositions comprising only of heteropoly acid and support material or only metal salt and support material at optimized conditions shows low isomerization activity as observed by low conversion percentage and disproportionate isomer ratio. However, surprisingly, catalyst combinations comprising of metal salt, heteropoly acid and support material shows high isomerization activity as observed by high conversion percentage and proportionate isomer ratio. Further, it is observed that certain combinations of metal salt, heteropoly acid and support material with specific percentages shows better result as compared to others. For example, the catalyst composition comprising of 5% Ni, TPA (30) and MOR (100) shows high isomerization activity than catalyst compositions comprising of lower percentages of Ni or TPA or MOR or catalyst compositions comprising of different heteropoly acid or support material as seen in example of heteropoly acid as MPA and support material as $TiO_2$.

Evaluation conditions were further varied and one of the catalysts was tested under a $H_2$ flow rate of 7 ml/min as well as 35 ml/min. n-hexane was used as the feed, temperature was kept constant at 250° C., pressure at 30 bars and WHSV at 2 $hr^{-1}$. At low hydrogen flow rates the catalyst showed better isomerization activity. Table 3 shows the effect of low hydrogen flow rates on isomerization activity of the catalyst, wherein MOR stands for mordenite, TPA stands for tungstophosphoric acid, 22DMB stands for 2,2-dimethylbutane, and 23DMB stands for 2,3-dimethylbutane.

TABLE 3

| S. No. | Catalyst | $H_2$ Flow (ml/min) | Conversion (%) | Selectivity (%) | 22DMB iso ratio | 23DMB iso ratio |
|---|---|---|---|---|---|---|
| 18 | 5% Ni-TPA(30)-MOR(100) | 35 | 11.35 | 96.82 | 6.16 | 13.52 |
| 19 | 5% Ni-TPA(30)-MOR(100) | 7 | 21.32 | 82.65 | 8.17 | 12.9 |

As seen in Table 3, by decreasing the hydrogen flow rate in the reactor and keeping other conditions constant the isomerization activity of the catalyst composition increases as observed by greater conversation percentage and proportionate isomer ratio. However, selectivity has decreased with the decrease in the hydrogen flow rate.

Evaluation conditions were further varied and one of the catalysts was tested under a 35 bar as well as 20 bar. n-hexane was used as the feed, temperature was kept constant at 250° C., $H_2$ flow was kept 35 ml/min and WHSV at 2 $hr^{-1}$. Table 4 shows the effect of pressure on isomerization activity of the catalyst, wherein MOR stands for mordenite, TPA stands for tungstophosphoric acid, 22DMB stands for 2,2-dimethylbutane, and 23DMB stands for 2,3-dimethylbutane.

TABLE 4

| S. No. | Catalyst | Pressure (bar) | Conversion (%) | Selectivity (%) | 22DMB iso ratio | 23DMB iso ratio |
|---|---|---|---|---|---|---|
| 18 | 5% Ni-TPA(30)-MOR(100) | 35 | 53.239 | 95.049 | 5.2032 | 6.3838 |
| 20 | 5% Ni-TPA(30)-MOR(100) | 20 | 21.132 | 82.647 | 1.5866 | 2.5076 |

As seen in Table 4, by decreasing the pressure in the reactor and keeping other conditions constant the isomerization activity of the catalyst composition decreases as observed by lesser conversation and selectivity percentage, and disproportionate isomer ratio.

From the above data it can be inferred that all catalyst compositions do not show high isomerization activity and the surprisingly and unexpectedly high isomerization activity is seen only with certain catalyst compositions of the present disclosure.

Advantages Gained in the Example Illustrative Compositions of this Subject Matter:

The above data indicates that, increasing the metal content deviant from the normal can decrease the conversion and selectivity of the catalyst. Thus all weight concentrations of the metal in the catalyst compositions do not show high isomerizing activity. Catalyst compositions with certain weight concentrations of the metal in the heteropoly acids can yield maximum conversion without loss of metal and show high isomerizing activity. Moreover, surprisingly and unexpectedly, it is found that catalyst compositions containing more than 20% support material exhibits overall high conversion rate and selectivity, which is contrary to the results of a study by Pérez-Luna et al. showing that catalyst compositions containing support material, i.e., alumina at a weight percentage higher than 20% reduce overall conversation rates and modify selectivity.

Although the subject matter has been described in considerable detail with reference to certain examples and implementations thereof, other implementations are possible. As such, the spirit and scope of the appended claims should not be limited to the description of the preferred examples and implementations contained therein.

What is claimed is:

1. A catalyst composition comprising:
   at least one metal, the at least one metal including Ni in an amount in the range of 0.1% to 10% w/w of the total weight of the composition;
   at least one heteropoly acid, the at least one heteropoly acid including tungstophosphoric acid in an amount in the range of 14% to 50% w/w of the total weight of the composition; and a support material, the support material including mordenite in an amount in the range of 60% to 85% w/w of the total weight of the composition.

2. The catalyst composition as claimed in claim 1, wherein the Ni is in an amount in the range of 0.1% to 6% w/w of the total weight of the composition.

3. The catalyst composition as claimed in claim 1, wherein the Ni is in an amount in the range of 1.5% to 6% w/w of the total weight of the composition.

4. The catalyst composition as claimed in claim 1, wherein the at least one metal is selected from the group consisting of alkali metal, alkaline earth metal, transitional metal, lanthanides, and combinations thereof.

5. The catalyst composition as claimed in claim 1, wherein the at least one metal further includes a alkali metal selected from the group consisting of Na, K, Rb, Cs, and combinations thereof.

6. The catalyst composition as claimed in claim 1, wherein the at least one metal is a transitional metal selected from the group consisting of Pt, Ni, Pd, Re, Ir, Rh, and combinations thereof.

7. The catalyst composition as claimed in claim 1, wherein the tungstophosphoric acid is in an amount in the range of 18% to 30% w/w of the total weight of the composition.

8. The catalyst composition as claimed in claim 1, wherein the at least one heteropoly acid is selected from the group consisting of tungstophosphoric acid (TPA), molybdophosphoric acid (MPA), and combinations thereof.

9. The catalyst composition as claimed in claim 1, wherein mordenite is in an amount in the range of 70% to 80% w/w of the total weight of the composition.

10. The catalyst composition as claimed in claim 1, wherein the support material further includes a material selected from the group consisting of alumina, zirconia, titania, silica, niobia, zeolites, mesoporous oxides, microporous oxides, ceria, vanadia, magnesia, yttria, and mesoporous materials selected from the group consisting of MCM-41, MCM-48, and SBA-15.

11. The catalyst composition as claimed in claim 1, wherein the support material further includes a zeolite selected from the group consisting of USY-zeolite, ZSM-5, ZSM-11, and beta zeolite.

12. The catalyst composition as claimed in claim 1, wherein the mordenite is in an amount in the range of 70% to 80% w/w of the total weight of the composition.

13. The catalyst composition as claimed in claim 1, wherein the catalyst composition is 1.5% to 6% w/w Ni, 18% to 30% w/w tungstophosphoric acid (TPA), and 70% to 80% w/w mordenite.

14. The catalyst composition as claimed in claim 1, wherein the catalyst composition is used for isomerization of paraffins.

15. A process for producing the catalyst composition as claimed in claim 1, the process comprising; dissolving at least one metal salt including the Ni in water to obtain a solution; contacting the at least one heteropoly acid including the tungstophosphoric acid and the support material including the mordenite with the solution to obtain a paste; drying the paste to obtain a dried paste; calcining the dried paste at a temperature range of 400-600° C. for a period of 1 to 6 hours to obtain a catalyst composition.

16. The process as claimed in claim 15, wherein the at least one metal salt including the Ni is a salt of Ni selected from the group consisting of nickel nitrate, nickel chloride, nickel acetate, nickel sulphate, and nickel acetylacetonate.

17. The process as claimed in claim 15, wherein the at least one metal salt further includes a salt of Pt selected from the group consisting of platinum nitrate, platinum chloride, platinum acetate, chloroplatinic acid, and platinum complexes such as hexamine platinum II chloride.

18. The process as claimed in claim 15, wherein the at least one metal salt further includes a salt of Cs selected from the group consisting of cesium nitrate, cesium chloride, cesium acetate, and cesiumsulfate.

19. The process as claimed in claim 15, wherein the at least one heteropoly acid further includes molybdophosphoric acid (MPA).

20. The process as claimed in claim 15, wherein the support material further includes a material selected from the group consisting of alumina, zirconia, titania, silica, niobia, zeolites, and mesoporous or microporous oxides.

21. The process as claimed in claim 20, wherein the support material further includes titania.

22. The process as claimed in claim 15, wherein the support material further includes a zeolite selected from the group consisting of USY-zeolite, ZSM-5, ZSM-11, and beta zeolite.

23. A process for producing a catalyst composition comprising; dissolving nitrate salt of Ni in water to obtain a solution; contacting tungstophosphoric acid (TPA), and mordenite with the solution to obtain a paste; drying the paste in vacuum at 70° C. for 1 hr at 100 mbar pressure to obtain a dried paste; calcining the dried paste at 300° C. for 4 h to obtain a catalyst composition; and the catalyst composition including the Ni in an amount in the range of 0.1% to 10% w/w of the total weight of the composition, the tungstophosphoric acid in an amount in the range of 14% to 50% w/w of the total weight of the composition, and the mordenite in an amount in the range of 60% to 85% w/w of the total weight of the composition.

24. A process for isomerization of paraffins comprising contacting the paraffins and hydrogen with a catalyst composition in a reactor; wherein the catalyst composition comprises Ni in an amount in the range of 0.1% to 10% w/w of the total weight of the composition; at least one heteropoly acid, the at least one heteropoly acid including tungstophosphoric acid in an amount in the range of 14% to 50% w/w of the total weight of the composition; and a support material, the support material including mordenite in an amount in the range of 60% to 85% w/w of the total weight of the composition.

25. The process as claimed in claim 24, wherein the at least one heteropoly acid further includes molybdophosphoric acid (MPA).

26. The process as claimed in claim 24, wherein the support material further includes alumina, zirconia, titania, silica, niobia, zeolites, mesoporous oxides, microporous oxides, ceria, vanadia, magnesia, yttria, and mesoporous materials selected from the group consisting of MCM-41, MCM-48, and SBA-15.

27. The process as claimed in claim 24, wherein the catalyst composition includes 1.5% to 6% w/w of the Ni, 18% to 30% w/w of the tungstophosphoric acid, and 70% to 80% w/w of the mordenite.

28. The process as claimed in claim 24, wherein the paraffin is a refinery feedstock such as straight run naphtha, cracked run naptha and fcc naphtha.

29. The process as claimed in claim 28, wherein the paraffin is $C_5$ to $C_{10}$ linear paraffin.

30. The process as claimed in claim 24, wherein hydrogen is passed over the catalyst composition at a rate of 10-100 mL/min.

31. The process as claimed in claim 24, wherein the process is carried out at a temperature in the range of 150-300° C.

32. The process as claimed in claim 24, wherein the process is carried out at a pressure in the range of 5-50 bar.

33. The process as claimed in claim 24, wherein the paraffin weight hourly space velocity is in the range of 0.01 to 100 hr$^{-1}$.

* * * * *